United States Patent [19]
De Haen et al.

[11] Patent Number: 5,587,487
[45] Date of Patent: Dec. 24, 1996

[54] TETRAIODOPYRROLE DERIVATIVES AS CONTRAST MEDIUM AND AS ANTISEPTIC

[75] Inventors: Christoph De Haen, Peschiera Borromeo; Fulvio Uggeri, Codogno; Ornella Gazzotti, Pianengo; Marino Brocchetta, Pavia, all of Italy

[73] Assignee: Dibra S.p.A., Milan, Italy

[21] Appl. No.: 448,510

[22] PCT Filed: Dec. 16, 1994

[86] PCT No.: PCT/EP94/04201

§ 371 Date: May 25, 1995

§ 102(e) Date: May 25, 1995

[87] PCT Pub. No.: WO95/17380

PCT Pub. Date: Jun. 29, 1995

[30] Foreign Application Priority Data

Dec. 23, 1993 [IT] Italy .................. MI93A2718

[51] Int. Cl.$^6$ .............................. C07D 207/305
[52] U.S. Cl. .................. 548/561; 548/413; 548/518; 548/531; 548/538; 548/560; 548/562
[58] Field of Search .................... 548/413, 518, 548/531, 538, 560, 561, 562

[56] References Cited

U.S. PATENT DOCUMENTS 5,371,239 12/1994 Doscher .................... 548/561

FOREIGN PATENT DOCUMENTS 0050457 4/1982 European Pat. Off. .

Primary Examiner—Joseph McKane
Attorney, Agent, or Firm—Bucknam and Archer

[57] ABSTRACT

The present invention refers to new contrast media particularly suited for X-ray diagnostic procedures of the human and animal body and also to the new compounds of general formulae (I) and (II).

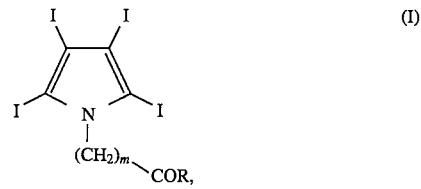

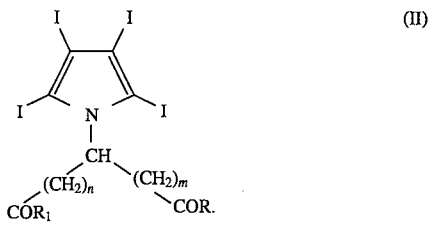

1 Claim, No Drawings

TETRAIODOPYRROLE DERIVATIVES AS CONTRAST MEDIUM AND AS ANTISEPTIC

This application is a 371 of PCT/EP 94/04201 filed Dec. 16,1994.

X-ray imaging is a widely used diagnostic technique for an early detection of a series of anomalies and/or pathological conditions in living tissues.

A better enhancement of images obtained through this diagnostic procedure was made possible thanks to contrast media of suitable opacifying agents. These compounds became unavoidable in the study of some organs or anatomical districts, characterised by a very low absorbing power with regard to radiations which were used and therefore unable to supply clear and sharp radiographic images.

Today's contrast media preferably contain, as opacifying molecules, neutral polyiodinated aromatic compounds (an extensive and up-dated publication on the state of the art of these diagnostic agents is the work of D. P. Swanson et al. "Pharmaceuticals in Medical Imaging", 1990, Mac Millan Publ. Company). The characteristic of these products relies on the inclusion of at least one benzene nucleus where three hydrogen atoms are replaced by three iodine atoms. An acceptable absorption of X-rays requires an iodine high concentration and therefore the above mentioned contrast agents have to be used in highly concentrated solutions.

The present invention refers to new contrast media particularly suited for X-ray diagnostic procedures of the human and animal body and also to the new compounds of general formulae (I) and (II)

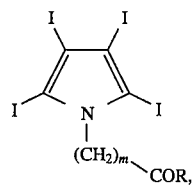

(I)

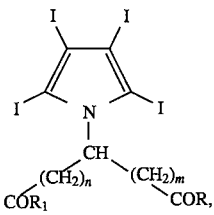

(II)

wherein:
m and n can independently vary between 0 and 5,
R can be H, —OR$_2$, —NR$_3$R$_4$, wherein
R$_2$ is H, straight or branched (C$_1$–C$_8$) alkyl, straight or branched (C$_1$–C$_8$) hydroxyalkyl with 1–7 —OH groups, or polyoxalkyl group of formula

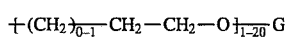

wherein G is H, CH$_3$, CH$_2$CH$_3$,
R$_3$ and R$_4$ which are the same or different, have the same meanings as R$_2$, or they are a group of formula —(CH$_2$)$_{1-2}$R$_5$ where R$_5$ can be one of the following groups COOH, SOH, SOH, POH, PO$_2$H or a derivative thereof, or they are a group of formula —CH$_2$CH$_2$R$_6$ where R$_6$ is a quaternary ammonium group of aliphatic or aromatic nature, or a group of formula

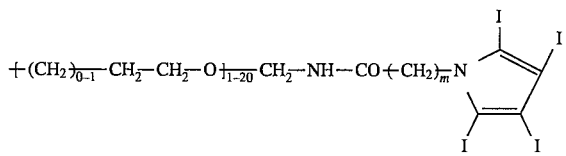

wherein m has the above meanings, or again R hd 3and R$_4$ can be a neutral or ionic organic residue containing from one to two triiodinated aromatic nuclei, or R$_3$ and R$_4$, considered together, can be a (C$_3$–C$_7$) residue, possibly interrupted by atoms of, S, N, or possibly substituted by hydrophilic and/or radiopaque functional groups,
R$_1$ has the same meanings as R and can be different or the same as R.

Should the compounds of formula (I) and (II) contain carboxylic and/or free phenol functions, this invention also include the salts of said compounds with physiologically acceptable organic bases, preferably selected among primary, secondary or tertiary amines, or basic amino acids, or with inorganic bases whose cations are sodium, potassium, magnesium, calcium or their mixtures.

Should compounds of formula (I) and (II) contain cationic functions, this invention also includes the salts of said compounds with anions of physiologically acceptable organic acids such as acetate, fumarate, succinate, oxalate, citrate, glutamate, aspartate or with anions of inorganic acids, such as chlorides, bromides, iodides or sulfates.

The new pyrrole derivatives of this invention are characterised in that they have four iodine atoms substituting the corresponding hydrogens. This substitution leads to a 89% iodine concentration, in the specific case of tetraiodopyrrole. Such a high iodine concentration allows the administration of the compounds of the invention at a lower concentration, thus reducing the chances of possible undesired side effects.

Up to now tetraiodopyrrole derivatives have never been used as X-ray contrast media, nor their use with this techniques has been mentioned or anticipated by the known prior art. On the contrary, in the past century tetraiodopyrrole was found to be an effective mean against syphilis, angina pectoris, diabetes and so on, thanks to its therapeutic characteristics,.

In patent literature, two patents, issued at the end of the last century, claim the tetraiodopyrrole preparation (or Iodol$^R$). The first patent concerns the direct pyrrole iodination with KI and KIO$_3$, while the second one refers to the reaction of the analogue tetrabromo and tetrachloro pyrroles with KI (Ciamician and Silber, U.S. Pat. No. 35130 D.R.P.; Kalle & co., U.S. Pat. No. 38423 D.R.P.).

Patent application EP-A-50457 (Population Res. Inc.) claims radiopaque polymeric compounds containing a mixture of a) an ester of 2-cyanoacrylic acid, b) a stable radiopaque additive, selected from iodocarboxylic acid, iodophenols, iodomethanes, iodothiophenes, iodoamines, and so on. 40 Specific additives are claimed, including N-methyltetraiodopyrrole. The molar percentage of iodine in mixtures a) and b) is 4–6%. Additives allow an in situ inspection of adhesive cyanoacrylated joints and can be used for industrial and medical applications, in particular welds and internal seams, e.g. of arteries or intestines, or female sterilisation plugs, without re-opening the patient [in the corresponding European patent only iodoform and tri-iodophenol, the sole specifically disclosed, have been accepted as radiopaque additives ].

The products of this invention are characterised by an high solubility, low viscosity and osmolality as well as a good tolerability.

In addition, the compounds of this invention, in view of their most suited diagnostic use, can be also bound or incorporated into biomolecules or macromolecules, able to selectively concentrate in the organ or the tissue under examination. Organ selectivity can also be obtained through the incorporation of said compounds in liposomes.

These compounds can be extensively used, since their administration can be intravasal, (for instance i.v., intraarterial, intracoronaric, intraventricular and so on), intrathecal, intraperitonal, intralymphatic, intracavital and intraparenchymal. Both soluble and less soluble compounds are suitable for oral or enteral administration, and therefore in particular for gastrointestinal tract (GI) imaging. As far as parenteral administration is concerned, they are preferably formulated as aqueous sterile solutions or suspensions, whose pH can vary i.e. between 6.0 and 8.5, possibly thanks to the use of physiologically acceptable basic buffer solutions (i.e. tris[hydroxymethyl]aminomethane or TRIS).

Said formulation can be provided in a lyophilized form to be reconstituted before use. In GI imaging or in body cavities injections, these agents can be formulated as a solution or suspension containing those additives producing i.e. a viscosity increase.

In oral administration, the compounds of the invention can be formulated according to preparation methods commonly used in the pharmaceutical technique: excipients, such as sweeteners or flavouring agents, can also be added according to known pharmaceutical formulation techniques.

Solutions or suspensions of complex salts can be also formulated as aerosol useful for aerosol-broncography.

Moreover, the compounds of this invention have shown some extremely interesting antiseptic properties which make them useful both for topical use and in particular for the sterilisation of medical apparatus (i.e. endoscopes and so on).

Therefore, one of the characteristic aspects of this invention is the possible use of compounds of general formula (I) and (II), as an effective alternative to compositions commonly used for said aim in the medical field.

The following experimental examples are aimed at showing the best experimental conditions to obtain the compounds of the invention and are in no way limiting.

EXAMPLE 1

2,3,4,5-tetraiodopyrrol-1-acetic acid

A) 2,3,4,5-Tetraiodopyrrole

A solution of 232.4 g of $I_2$ (0.9156 mol) and 364.7 g of KI (2.197 mol) in 2300 mL of $H_2O$ is dropwise added, in about 2 h, to a solution of 15.36 g of pyrrole (commercial product) (0. 2289 mol) in 536.6 mL of 5M NaOH (2.683 mol) under stirring at 5°–10° C. After 1 h at the same temperature and one night at room temperature, the reaction mixture is acidified to pH 2.5 with 146.33 mL of 37% HCl (w/w) (1.7672 mol). The precipitate is filtered and washed with $H_2O$, then dissolved in acetone and treated with carbon Carbopuron 4N. The solution is filtered and evaporated under reduced pressure and the residue crystallizes upon heat treatment with abs. EtOH. The precipitate is filtered, washed with abs. EtOH and dried. 94.00 g of 2,3,4,5-tetraiodopyrrole (0.1647 mol) are obtained.
Yield 72% m.p.: 150° C. (dec.)
HPLC: 99.8% (% in area)

| | Elemental analysis | | | | |
|---|---|---|---|---|---|
| | C | H | I | N | |
| % calc.: | 8.42 | 0.18 | 88.95 | 2.45 | |
| % found: | 8.37 | 0.18 | 86.32 | 2.45 | $H_2O < 0.1$ |

TLC: silica gel plate 60F 254 Merck
Eluent: n-hexane: AcOEt =8: 2 (v/v)
Detector: 1% $KMnO_4$ in 1N NaOH $R_f$=0.50 $^1$H-NMR, $^{13}$C-NMR, IR and MS spectra are in accordance with the indicated structure.

B) 2,3,4,5-Tetraiodopyrrol-1-acetic acid ethyl ester

To a solution of 22.9 g of compound A), 2,3,4,5-tetraiodopyrrole (40.13 mmol), in 170 mL of DMF, 16.05 mL of 2.5 M MeONa in MeOH (40.13 mmol) are added under stirring for 15 min in nitrogen atmosphere. MeOH is removed under reduced pressure and 10 g of ethyl iodoacetate (product instantly prepared from $BrCH_2COOEt$ and 4 KI equivalents in acetone) (46.73 mmol) are dropwise added (30 min) to the residue. The solution is kept at room temperature for 1.5 h. After dilution with $H_2O$, an intensely coloured solid precipitates, then is filtered, redissolved in DMF and treated with carbon Carbopuron 4N. The solution is filtered, concentrated to dryness and crystallized from abs. EtOH, to obtain 20 g of 2,3,4,5-tetraiodopyrrol-1-acetic acid (30.45 mmol) ethyl ester.
Yield: 76% m.p.: 216° C.
HPLC: 100% (% in area)
Stationary phase: Column E. Merck Superspher RP18 mm 250 ×4 mm;
Mobile phase: Gradient elution;

| A = 0.01 M $KH_2PO_4$ aqueous solution | | | |
|---|---|---|---|
| B = $CH_3CN$ | min | % A | % B |
| | 0 | 72 | 28 |
| | 10 | 72 | 28 |
| | 20 | 50 | 50 |
| | 50 | 50 | 50 |
| | 52 | 72 | 28 |

Flow: 1.5 mL min-1;
Temperature: 40° C.; (UV) detector: 220 nm.

| | Elemental analysis: | | | | |
|---|---|---|---|---|---|
| | C | H | I | N | |
| % calc.: | 14.63 | 1.07 | 77.29 | 2.13 | |
| % found: | 14.65 | 1.05 | 77.01 | 2.13 | $H_2O < 0.1$ |

TLC: silica gel 60F 254 Merck
Eluent: n-hexane: AcOEt =8: 2 (v/v) Detector: 1% $KMnO_4$ in 1N NaOH $R_f$=0.55 $^1$H-NMR, $^{13}$C-NMR, IR and MS spectra are in accordance with the indicated structure.

C) 2,3,4,5-tetraiodopyrrol-1-acetic acid

TO a solution of 23.2 g of compound B), 2,3,4,5-tetraiodopyrrol-1-acetic acid ethyl ester (35.32 mmol) , in 840 mL of a dioxane (750 mL) / $H_2O$ (90 mL) mixture, 36 mL of 1M NaOH (36 mmol) are quickly added (10 min) and the final solution is kept at room temperature for 4 h. The reaction mixture is treated with carbon Carbopuron 4N, filtered, then acidified with 37% HCl (w/w) and diluted in 500 l of $H_2O$, to give a solid which is filtered and purified by chromatography (silica gel (product E. Merck item 9385): eluent: $CHCl_3$ : MeOH : 25% $NH_4OH$ (w/w) =7.5:2:0.3 (v/v/v)). Fractions with similar purity are collected, evaporated and diluted with 200 mL of $H_2O$. By acidifying the aqueous phase with 40 mL of 1M HCl, a solid precipitates, which is filtered, washed with $H_2O$ and dried under reduced pressure. 21.5 g of 2,3,4,5-tetraiodopyrrol-1-acetic acid(34.20 mmol) are obtained.

Yield: 95% m.p.: 153° C. (dec.)
HPLC: 100% (in area %)
Stationary phase: Column E. Merck Superspher RP-18 mm 250 ×4 mm;
Mobile phase: gradient elution;

| A = 0.01 M $KH_2PO_4$ aqueous solution<br>B = $CH_3CN$ | min | % A | % B |
|---|---|---|---|
| | 0 | 72 | 28 |
| | 10 | 72 | 28 |
| | 20 | 50 | 50 |
| | 50 | 50 | 50 |
| | 52 | 72 | 28 |

Flow: 1.5mL . min-1;
Temperature: 40 ° C.;
(UV) detection: 220 nm.

| | Elemental analysis | | | |
|---|---|---|---|---|
| | C | H | I | N |
| % calc.: | 11.46 | 0.48 | 80.74 | 2.23 |
| % found: | 11.43 | 0.47 | 79.56 | 2.24 | $H_2O$ < 0.1 |

TLC: silica gel plate 60F 254 Merck
Eluent: $CHCl_3$: MeOH : 25% $NH_4OH$ (w/v)=7.5: 2 : 0.3
Detector: 1% $KMnO_4$ in 1N NaOH $R_f$=0.26 $^1$H-NMR, $^{13}$C-NMR, IR and MS spectra are in accordance with the indicated structure.

EXAMPLE 2

N-[2-hydroxyethoxy)ethyl]-2,3,4,5,-tertraiodopyrrol-1-acetamide.

1.56 g of 2,3,4,5-tetraiodopyrrol-1-acetic acid ethyl ester (prepared according to the procedure described in Ex. 1) (2.37 mmol) and 7.49 g of 2-(2-amminoethoxy)ethanol (commercial product) are mixed and heated to 80° C. to obtain complete dissolution after 1.5 h. EtOH formed during the reaction is directly evaporated under vacuum. After 4h the reaction is completed. The solution is dissolved in water and the desired product precipitates, then is filtered, washed and dried. 1.5 g of N-[2-(2-hydroxyethoxy)ethyl]-2,3,4,5,-tetraiodopyrrol-1-acetamidc (2.09 mmol) are obtained.
Yield: 88%

| | Elemental analysis | | | |
|---|---|---|---|---|
| | C | H | I | N |
| % calc.: | 16.78 | 1.69 | 70.91 | 3.91 |
| % found: | 16.50 | 1.70 | 69.56 | 3.89 |

TLC: silica gel plate 60F. 254 Merck
Eluent: $CHCl_3$ : MeOH : $NH_4OH$ =9 : 1.2 : 0.3

Detector: 1% $KMnO_4$ in 1N NaOH $R_f$=0.53 $^1$H-NMR, $^{13}$C-NMR, IR and MS spectra are in accordance with the indicated structure.

EXAMPLE 3

N-[3,6,9,12,15,18,21-heptaoxadocos-1-yl]-2,3,4,5-tetraiodopyrrol-1-1-acetamide

A) 4-nitrobenzenesulfonic acid 3,6,9,12,15,18,21-heptaoxadocos-1-yl ester 6.7 g of triethylamine (TEA) (0.06 mol) are dropwise added, in 10 minutes, to a solution of 20.4 g of 4-nitrobenzenesulfonyl chloride (obtained according to the procedure described by F. Gialdi, R. Ponci , "Il Farmaco" Vol XIV, 751, 1959) (0.06 mol) and 20.4 g of 3,6,9,12,15,18,21-heptaoxadocosan-1-ol (obtained according to the procedure described in Liebigs Ann. Chem. 1980, 858–862 ) (0.06 mol) in 60 mL of AcOEt.

After 2 h at a temperature of 20° C., the precipitated TEA hydrochloride is washed for three times with 10-mL portion of AcOEt, then filtered off.

The filtrates are collected, washed with 30 mL of $H_2O$, 20mL of 2N HCl and then with H2O up to neutrality.

The organic phase is concentrated to dryness, to obtain a thick oil which is directly used in the following step with no other purification. 25 g of 4 -nitrobenzenesulfonic acid 3,6,9,12,15,18,21-heptaoxadocos-1-yl ester (0,047 tool) are obtained.
Yield: 79 %
TLC: silica gel plate 60F 254 Merck
Eluent: MeOH
Detector: UV light (254 nm) $R_f$=0.76 $_1$ H-NMR, $^{13}$C-NMR IR and MS spectra are in accordance with the indicated structure.

B) 3,6,9,12,15,18,21-heptaoxadocosylamine 9.2 g of compound A), 4-nitrobenzenesulfonic acid 3,6,9,12,15,18,21-heptaoxadocos-1ester (0.0175 mol), are diluted in NH40H at 60° C. in 10 minutes. After 2.5 h at 60° C., the solution is cooled and the $NH_4OH$ excess is evaporated, the crude is diluted in 70 mL of $H_2O$ and percolated on a cation exchange resin Duolite$^R$ C20MB. The eluate is concentrated under reduced pressure and the crude is purified by means of flash chromatography.

3,3 g of 3,6,9,12,15,18,21-heptaoxadocosylamine (0.0098 mol) are obtained.
Yield: 56%
TLC: silica gel plate 60F 254 Merck
Eluent: $CHCl_3$:MeOH:NH4OH =9:1.2:0.2
Detector: solution of ninhydrin 0.2% in EtOH $R_f$=0.42
$^1$H-NMR, $^{13}$C-NMR, IR and MS spectra are in accordance with the indicated structure.

C) N-[3,6,9,12,15,18,21-heptaoxadocos-1-yl]-2,3,4,5-tetraiodopyrrol-1 -acetamide According to the procedure described in Ex. 2, 2.3 g of 2,3,4,5-tetraiodopyrrol-1-acetic acid ethyl ester (prepared according to the procedure described in Ex. 1) (0.00457 mol) and 23.27 g of compound B, 3,6,9,12,15,18,21-heptaoxadocosylamine, (0.0685 mol) are reacted. 3.82 g of N-[3,6,9,12,15,18,21-heptaoxadocos-1-yl]-2,3,4,5-tetraiodopyrrol-1-acetamide (0.0040 mol) are obtained.

Yield: 88%

| | Elemental analysis | | | |
|---|---|---|---|---|
| | C | H | I | N |
| % calc.: | 26.55 | 3.61 | 53.43 | 2.95 |
| % found: | 26.49 | 3.59 | 52.87 | 2.89 |

$^1$H-NMR, $^{13}$C-NMR, IR and MS spectra are in accordance with the indicated structure.

EXAMPLE 4

The antiseptic activity of 2,3,4,5-tetraiodopyrrol-1-acetic acid, prepared according to Example 1, was studied on a number of Gram+ and Gram− microorganisms as well as on fungi. The tested compound showed both bacteriostatic and bactericidal activity.

Bacteriostatic Activity

Minimal inhibiting concentration (MIC) obtained on the Gram+ microorganisms of reference ranged from 0.1 to 0.4 rag(compound)/mL.

MIC obtained on the Gram− microorganisms of reference ranged from 1.6 to 25.6 mg(cpd)/mL. MIC obtained on fungi of reference ranged from 1.6 to 3.2 mg(cpd)/mL.

Bactericidal Activity

Minimal bactericidal concentration (MBC) obtained on the Gram+ microorganism of reference ranged from 0.4 to 1.6 mg(cpd)/mL MBC obtained on the Gram− microorganism of reference ranged from 1.6 to 2 5.6 mg(cpd) /mL MBC obtained on fungi of reference ranged from 1.6 to 3.2 mg(cpd)/mL.

We claim:

1. A compound of general formulae (I) and (II)

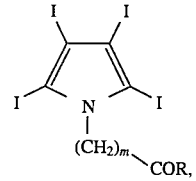

(I)

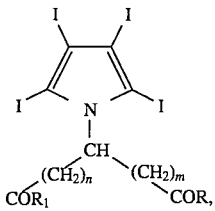

(II)

wherein:

m and n are independently between 0 and 5,

R is H, —$OR_2$, —$NR_3R_4$, wherein $R_2$ is H, straight or branched ($C_1$–$C_8$) alkyl, straight or branched ($C_1$–$C_8$) hydroxyalkyl with 1—7 -OH groups, or polyoxalkyl group of formula $$\text{—}(CH_2)_{\overline{0\text{-}1}}\text{—}CH_2\text{—}CH_2\text{—}O\,]_{\overline{1\text{-}20}}\,G$$

wherein G is H, $CH_3$, $CH_2CH_3$, $R_3$ and $R_4$ which are the same or different, have the same meanings as $R_2$, or they are a group of formula —$(CH_2)_{1-2}R_5$ where $R_5$ is one of the following groups COOH, $SO_3H$, $SO_2H$, $PO_3H$, or $PO_2H$, or they are a group of formula —$CH_2CH_2R_6$ where $R_6$ is a quaternary ammonium group of aliphatic or aromatic nature, or a group of formula $$\text{—}(CH_2)_{\overline{0\text{-}1}}\text{—}CH_2\text{—}CH_2\text{—}O\,]_{\overline{1\text{-}20}}\,CH_2\text{—}NH\text{—}CO\text{—}(CH_2)_{\overline{m}}\,N\underset{I}{\overset{I}{\diagdown}}\underset{I}{\overset{I}{\diagup}}$$

wherein m has the above meanings, or $R_3$ and $R_4$ are a neutral or ionic organic group containing from one to two triiodinated aromatic nuclei, or $R_3$ and $R_4$, considered together, are a ($C_3$–$C_7$) group, optionally interrupted by atoms of 0, S, N, or optionally substituted by hydrophilic or radiopaque functional groups, $R_1$ has the same meanings as R and is different or the same as R, and in case the compounds of formulae (I) and (II) contain free carboxylic and/or phenol functions, also the salts of said compounds with physiologically acceptable organic bases which are selected from primary, secondary or tertiary amines, or basic amino acids, or with inorganic bases whose cations are sodium, potassium, magnesium, calcium or their mixtures and, in case compounds of formulae (I) and (II) contain cationic functions, also the salts of said compounds with anions of physiologically acceptable organic acids selected from acetate, fumarate, succinate, oxalate, citrate, glutamate, aspartate or with anions of inorganic acids selected from chlorides, bromides, iodides or sulfates.

* * * * *